United States Patent
Juneau et al.

(10) Patent No.: US 6,473,512 B1
(45) Date of Patent: Oct. 29, 2002

(54) APPARATUS AND METHOD FOR A CUSTOM SOFT-SOLID HEARING AID

(75) Inventors: Roger P. Juneau, Destrehan; Lynn P. Creel, Kenner; Edward J. Desporte, Covington; Michael Major; Gregory R. Siegle, both of Kenner; Kelly M. Kinler, Luling, all of LA (US)

(73) Assignee: Softear Technologies, L.L.C., Harahan, LA (US)

( * ) Notice: Subject to any disclaimer, the term of this patent is extended or adjusted under 35 U.S.C. 154(b) by 0 days.

(21) Appl. No.: 09/181,845

(22) Filed: Oct. 28, 1998

Related U.S. Application Data

(63) Continuation-in-part of application No. 09/084,864, filed on May 26, 1998.
(60) Provisional application No. 60/068,035, filed on Dec. 18, 1997.

(51) Int. Cl.⁷ .............................................. H04R 25/00
(52) U.S. Cl. ......................... 381/328; 381/322; 381/328
(58) Field of Search ................................ 381/312, 322, 381/324, 325, 328, 380

(56) References Cited

U.S. PATENT DOCUMENTS

| | | | |
|---|---|---|---|
| 3,345,737 A | 10/1967 | Gordon ....................... 381/328 |
| 4,051,330 A | 9/1977 | Cole | |
| 4,375,016 A | 2/1983 | Harada | |
| 4,569,812 A | 2/1986 | Werwath et al. ............. 264/222 |
| 4,607,720 A | 8/1986 | Hardt | |
| 4,716,985 A | * 1/1988 | Haertl .......................... 181/130 |
| 4,811,402 A | * 3/1989 | Ward ........................... 181/130 |
| 4,834,927 A | 5/1989 | Birkholz et al. ............. 264/134 |
| 4,860,362 A | 8/1989 | Tweedle ...................... 381/322 |
| 4,870,688 A | * 9/1989 | Voroba et al. ................ 381/60 |
| 4,871,502 A | 10/1989 | Lebisch et al. ............. 264/222 |
| 4,880,076 A | * 11/1989 | Ahlberg et al. ............. 181/130 |
| 4,937,876 A | 6/1990 | Biërmans | |
| 5,002,151 A | * 3/1991 | Oliveira et al. ............. 181/130 |
| 5,008,058 A | 4/1991 | Henneberger et al. ...... 264/222 |
| 5,068,902 A | 11/1991 | Ward | |
| 5,185,802 A | 2/1993 | Stanton | |
| 5,201,007 A | 4/1993 | Ward et al. | |

(List continued on next page.)

FOREIGN PATENT DOCUMENTS

| | | |
|---|---|---|
| JP | 61-238198 | 10/1986 |
| WO | WO 93/25053 | * 12/1993 |

OTHER PUBLICATIONS

Oliveira, Robert J., "The Active Ear", *Journal of American Academy of Audiology*, Dec. 1997, pp. 401–410.

Staab, Wayne J. and Barry Finlay, "A fitting rationale for deep fitting canal hearing instruments", *Hearing Instruments*, vol. 42, No. 1, 1991, pp. 7–10, 48.

*Primary Examiner*—Curtis Kuntz
*Assistant Examiner*—P. Dabney
(74) *Attorney, Agent, or Firm*—Garvey, Smith, Nehrbass & Doody, L.L.C.; Seth M. Nehrbass; Charles C. Garvey

(57) ABSTRACT

An apparatus and method of manufacturing a soft-solid elastomer custom ear device into which electronics are embedded provides a completely in-the-ear hearing aid with a soft body. This technology replaces hard acrylic ear molding. This hearing aid by virtue of its soft-solid design, meets the needs of the dynamic human ear canal which cannot be met with conventional hard acrylic molding. This hearing aid provides improved comfort and sound quality by better adapting to the dynamic changes in the ear canal which occur during everyday activities. This soft custom body also provides for ear-worn configurations of all subminiature electronic devices requiring discrete coupling to the human ear. These devices include digital telephones, cellular telephones, pagers, two-way communication systems, clocks, recorders, and many other subminiature technologies.

50 Claims, 9 Drawing Sheets

U.S. PATENT DOCUMENTS

| | | |
|---|---|---|
| 5,259,032 A | 11/1993 | Perkins et al. |
| 5,319,163 A * | 6/1994 | Scott .......................... 181/130 |
| 5,357,786 A * | 10/1994 | Lung et al. .................... 73/81 |
| 5,430,801 A | 7/1995 | Hill |
| 5,500,902 A | 3/1996 | Stockham, Jr. et al. |
| 5,530,763 A | 6/1996 | Aebi et al. |
| 5,659,621 A | 8/1997 | Newton |
| 5,748,743 A * | 5/1998 | Weeks ....................... 381/68.6 |
| 5,917,918 A * | 6/1999 | Callahan ..................... 381/67 |
| 5,999,632 A * | 12/1999 | Leysieffer et al. .......... 381/328 |
| 6,022,311 A * | 2/2000 | Juneau et al. ................. 600/25 |

* cited by examiner

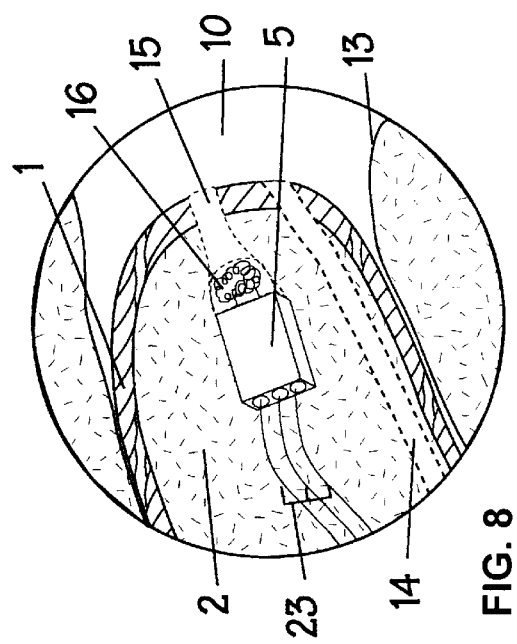
FIG. 7
FIG. 8
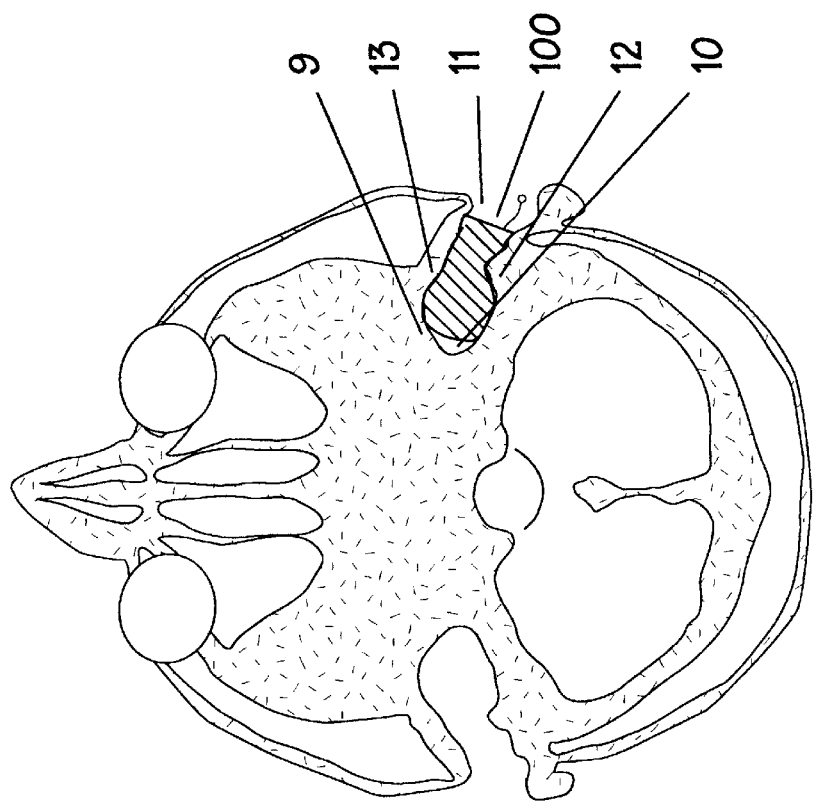
FIG. 6

APPARATUS AND METHOD FOR A CUSTOM SOFT-SOLID HEARING AID

CROSS-REFERENCE TO RELATED APPLICATIONS

This is a continuation-in-part of our co-pending U.S. patent application Ser. No. 09/084,864, filed May 26, 1998, and incorporated herein by reference.

Also incorporated herein by reference are all patent applications filed by us relating to hearing aid technology in October 1998.

Priority of U.S. Provisional Patent Application Serial No. 60/068,035, filed Dec. 18, 1997, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

I. Field of the Invention

The present invention relates to an ear-worn device that is comprised of a soft yet solid elastomer corpus for use in custom in-the-ear hearing products. The degree of stiffness of this soft-solid material preferably ranges from negligible to forty points, Durometer Hardness, Shore A. Specifically, the present invention relates to a system and method for producing a custom soft yet solid elastomer hearing product yielding greater comfort and superior acoustic performance for the hearing instrument wearer. Additionally, this product will provide solutions to a population with whom traditional custom in-the-ear technology was unsuccessful. By the nature of its soft design this product will have improved compliance and elasticity, thereby better accommodating the dynamic nature and the anatomical variants of the external ear canal. This invention will also relate to future applications in the field of mass communications, such as an ear-worn digital telephone or a two-way radio system.

II. General Background of the Invention

The Hearing Instrument Industry combines electro-acoustic technology with custom prosthetic design to ergonomically couple a hearing instrument to the human ear in a cosmetically acceptable manner. The industry has realized major electronic advancements in hearing instrument technology. With miniaturization of electronic components the standard instrument design evolved from a table worn unit, using vacuum tubes in the nineteen twenties, to a wearable body worn unit in the late nineteen thirties. The introduction of transistors in the nineteen fifties made the behind-the-ear (BTE) hearing instrument possible. As integrated circuits were developed, the custom in-the-ear (ITE) instrument became a reality. On-going electronic developments surrounding the hearing instrument industry have resulted in the micro-miniaturization of electronic components. This miniaturization has culminated in the introduction of "deep insertion technology", manifested as the completely-in-the-canal (CIC) hearing instrument, which is totally contained within the ear canal and is virtually invisible. As a consequence, hearing instruments have increased signal processing capabilities, yet require very limited physical space.

With the development of programmable hearing instruments, using either analog or digital signal processing, custom electronic design has shifted from the manufacturing level to the clinical level. That is, the clinician can now customize the electro-acoustic response of the instrument to match the degree of hearing loss via programmable software. It is no longer necessary for the device to be returned to the manufacturer for hardware changes to achieve the desired electro-acoustic characteristics.

In direct contrast to electronic advances within the industry, little or no advancement has been realized in custom prosthetic design. Since the late nineteen sixties, when the custom instruments were developed, the materials and the construction techniques have remained virtually unchanged. These materials and techniques were adopted from the dental industry, whereby the customized housing—commonly called a "shell"—was constructed using acrylic with a ninety point "D" Shore Hardness. Typical molding of the dental acrylate involves making a female silicone cavity from the original ear impression. This female cavity is then filled with liquid acrylate and cured using an ultraviolet light of known intensity across a known time period to cure only the outer most material forming a wall or a shell. This process is very similar to ceramics. The shell is then removed from the female cavity, decked down in the sagittal plane, drilled for vents and receiver bores, polished and then mounted with a faceplate containing the electro-acoustic circuitry. The end result is a hollow glass-like plastic replica of the external ear canal. The finished shell's primary function is to house the delicate electronic components. Yet, a material of this hardness, worn deeply in the human ear canal, brings forth the issues of comfort and acoustic performance.

When the acrylic shell was introduced, hearing instruments were worn in a relatively elastic cartilaginous portion of the ear canal. However, the current trend for hearing instrument placement is to position the device into the bony portion of the ear canal extending three millimeters medially from the second directional bend previously defined as "deep insertion technology". To illustrate the implications of this technology, the anatomy and physiology of the ear will be reviewed.

Anatomically, the ear canal is defined as the area extending from the concha to the tympanic membrane. It is important to note that the structure of this canal consists of elastic cartilage laterally, and porous bone medially covered by skin. The cartilaginous portion constitutes the outer one third of the ear canal. The medial two-thirds of the ear canal is osseous or bony and is oriented forward and downward making it slightly concave as compared to the more cylindrical cartilaginous portion. The average canal is approximately twenty-five millimeters in length but is as much as six millimeters longer on the anteroinferior wall of the osseous canal. The skin of the osseous canal, measuring only two-tenths of a millimeter (0.2 mm) in thickness, is much thinner than the skin of the cartilaginous canal, measuring five-tenths to one millimeter (0.5 to 1 mm) in thickness. The difference in thickness directly corresponds to the presence of apocrine (ceruminous) and sebaceous glands found only in the fibro-cartilaginous area of the canal. This thinly skinned, thinly lined area of the bony canal is extremely sensitive to any hard foreign body, such as an acrylic hearing instrument.

Physiologically, the ear canal is dynamic in nature. It is geometrically altered by mandibular action and by head position changes. These cause alternating elliptical elongation and widening of the ear canal. These alterations in canal shape vary widely, not only from person to person, but also from ear to ear.

Applying hard, hollow, acrylic hearing instrument technology to the external ear canal has numerous limitations. Because of the rigid nature of the acrylic shell of many traditional instruments, they are difficult to insert beyond the second directional canal bend. The difficulty of insertion is increased in the presence of any anatomical variant such as a stenotic canal, a bulbous canal, or a tortuous canal.

Because of the rigid nature of the acrylic shell of many traditional instruments, they must pivot in reaction to mandibular action or head movement, thereby changing the angle of attack of the receiver toward the tympanic membrane resulting in a distorted acoustic response.

Additionally, this pivoting action often causes displacement of the entire instrument causing a slit leak between the wall of the device and the wall of the ear canal. That leak creates an open acoustic loop between the receiver and the microphone of the instrument resulting in an electro-acoustic distortion commonly known as feedback.

Because of the rigid nature of the acrylic shell, some deeply inserted traditional instruments will exert pressure upon the bony portion of the ear canal when mandibular action or head movement cause the instrument to pivot.

Because of the hollow nature of the acrylic shell, many traditional instruments cannot protect the internal components from damage due to shock (i.e. the impact suffered by a traditional instrument dropped onto a hard surface).

Because of the hollow nature of the acrylic shell, many traditional instruments provide an air-conducted feedback loop from the receiver to the microphone.

Because of the hollow nature of the acrylic shell and the inherent necessity to suspend the receiver by tube mounting, the traditional instrument is prone to collection of cerumen in the receiver tube. Attempts to excavate the cerumen often breaks the bond between the receiver tube and the receiver port of the shell, displacing the receiver into the instrument.

Because of the solid nature of the acrylic shell, the proximal tip of many traditional instruments serves as a reverberating surface for acoustic energy reflected by the tympanic membrane resulting in distortion.

Because of the rigid and hollow nature of the acrylic shell, traditional instruments with such a shell have relatively widely separated interior surfaces that promote internal acoustic reverberation and its attendant feedback.

To compensate for these limitations, modification to the hard shell exterior to approximate the anatomical variants and to meet the demands of the dynamic nature of the ear canal are performed. The shell is buffed and polished until comfort is acceptable without significantly compromising acoustic performance. The peripheral acoustic leakage caused by these modifications often results in acoustic feedback (whistling) before sufficient amplification can be attained. Additionally, this acoustic leakage causes annoying low frequency sounds to be inadvertently amplified by means of a Helmholtz resonator. Patients commonly report this sensation as "My voice is hollow" or "My head sounds like it is in a barrel."

Another approach taken to compensate for the limitations of the hard, hollow acrylic shell has been to alter the electro-acoustic parameters of the instruments. It was expected that, with the development of programmable devices, a sophisticated, precise electro-acoustical method of eliminating these acoustic anomalies would be available to the clinician. Ironically, the improved frequency spectrum of the programmable instruments exacerbated the problem. The practical solution was to adjust the program of an instrument which was exhibiting feedback by reducing the high frequency information, or to retreat to a larger behind-the-ear hearing aid.

Faced with the limited success of shell or electro-acoustic modification, a few manufacturers have attempted all-soft shells. Wearers did report greater comfort and better sound quality. Unfortunately, while rigid acrylic does not lose its dimensional stability, soft vinyl materials shrink, discolor, and harden after a relatively short period of wear (the replacement of vinyl material used for BTE earmolds, for example, is recommended on at least a yearly basis). Polyurethane provides a better acoustic seal than polyvinyl, but has an even shorter wear life (approximately three months). Silicones have a long wear life but are difficult to bond to plastics, a necessary process for the construction of custom hearing instruments. Furthermore, silicone is difficult to modify when the dimensional structure requires alteration for proper fit. To date, then, acrylic has proven to be the only material with long term structural integrity. The fact remains, however, that the entire ear is a dynamic acoustic environment ill-served by a rigid material such as acrylic.

Some references of interest are discussed below. These references are all incorporated herein by reference.

U.S. Pat. No. 4,870,688 to Voroba, Barry, et al.

Voroba describes a patient selected mass produced, non-custom molded form fitting shell with a malleable covering having a hook and twist which in theory precisely conforms to the patient's own ear.

U.S. Pat. No. 4,880,076 to Ahlberg, Carl, et al.

Ahlberg discloses a user-disposable foam sleeve comprising a soft polymeric retarded recovery foam that can be compressed to be freely inserted into the patient's ear and then allowed to expand until secure in the ear canal.

Other patents that may be of interest include the following:

U.S. Pat. No. 5,002,151 to Oliveira, Robert J., et al.;

U.S. Pat. No. 4,607,720 HEARING AID;

U.S. Pat. No. 4,375,016 VENTED EAR TIP FOR HEARING AID AND ADAPTER COUPLER THEREFOR;

U.S. Patent Nos.: 4,051,330; 4,716,985; 4,811,402; 4,937,876; 5,068,902; 5,185,802; 5,201,007; 5,259,032; 5,530,763; 5,430,801; 5,500,902; and 5,659,621.

Also of interest and incorporated herein by reference are published Japanese patent application no. JA61-238198, the articles from December 1997 JOURNAL OF AMERICAN ACADEMY OF AUDIOLOGY, and Staab, Wayne J. and Barry Finlay, "A fitting rationale for deep fitting canal hearing instruments", HEARING INSTRUMENTS, Vol. 42, No. 1, 1991, pp. 7–10, 48.

BRIEF SUMMARY OF THE INVENTION

The present invention relates generally to in-the-ear hearing aids and particularly to a soft elastomer solid within which the electronic components are embedded. The hearing aids can be custom or mass produced. The general objective of this invention is to provide a product which is authentic to the shape of the external ear canal, yet compliant enough to compensate for the dynamic properties of the canal. In addition to that general objective, there are specific objectives. This objective is accomplished by providing a body which, in the preferred embodiment of the present invention, has a 5–15 durometer, Shore A hardness to optimize the following apparently opposing desired characteristics:

the device should be stiff enough to easily insert into the ear;

the device should be soft enough to compress and recover, once inserted into the ear, as the jaw's mandibular action flexes the external ear canal changing the horizontal diameter as it opens and closes; and the device should not tear or elongate during stretching to the point that the strain relief systems between the amplifier and receiver would be overly burdened to failure. i.e. wires or connections would not break when the device is flexed by tensile force, compression, torsion or a complex combination of the three forces.

The present invention includes an ear-worn hearing device a hearing device body sized and shaped to generally fit into a human ear canal; and an electronic hearing circuit embedded in the body, wherein the body is made of a soft-solid elastomer and the body has a Durometer Hardness, Shore A, of less than 40 points.

The body of the device of the present invention preferably comprises an elastomer blend which once completely vulcanized is bondable to another elastomer blend which has not been vulcanized and which is of similar elastomeric characteristics in the finished and unfinished state, both of which can be formulated at the very low end of the shore A scale (preferably ranging from 0–17 Durometer). This bonding capability will provide a platform for the resizing of an existing device and further provide the platform for the manufacture of a series of universal, non-custom, soft-solid devices. These universal devices could be customized by the manufacturer or at the clinic on a later date using a dipping process or some other external patching technique to bond the existing soft-solid device to a new outer layer of soft-solid elastomer. It is also possible to use this bonding process to bond a soft elastomeric outer layer to a universal shell made of traditional hard, hollow, acrylic shell material (though it would be preferred to fill this shell with elastomer to obtain the benefits of a solid device).

This bonding capability will provide the platform for the manufacture of a soft-solid device of two different designs. The first design would be similar to an M&M brand peanut candy, where the electronic components are the peanut. The inside chocolate would be made of elastomers which are stiff (27 Shore A Durometer, e.g.) to serve as a skeleton support for insertion into the ear. This center medium would be relatively thin compared to the candy, say 2 mm or less. The outer candy shell would be very soft (e.g. 7–10 Shore A Durometer) and would be thick, 3 mm or more as the size dictates.

The second design would be more like the candy model, in that the center would be very soft elastomer (3–10 Shore A Durometer, e.g.) and approximately 3–4 mm in thickness as the ear canal allows and outer shell would be approximately 27 Shore A Durometer, e.g., and for example 1 mm thick. In this design the insertion rigidity would be provided by the outer layer. The components in the inner layer would be embedded in soft elastomer allowing it to move more easily and would not bond the components as tightly reducing the conductive pathways between the receiver and other components.

Both of these approaches would allow the product to be inserted into the ear, maintain wall pressure on the ear canal wall, and allow the components to move with dynamic motion with the aid of a proper wire stain relief system described later herein.

The present invention, because of its soft nature, will not migrate out of the external ear canal with jaw excursion. It is resistant to the lateral migration which is innate to traditional non-compliant shell.

The present invention, by its soft nature, will remain authentic to the topography of the ear canal, and will remain acoustically sealed with jaw excursion. The acoustic seal will reduce the peripheral leakage, and allow for greater gain and sound pressure before feedback. Concomitant with the improved acoustic seal and the elimination of the slit leak, there will be greater mid-frequency amplification and the elimination of high frequency roll-off, thereby emphasizing those frequencies most important for the perception of consonantal cues.

A total of 24 patients (44 ears) have been fit with the soft-solid device for the purpose of pilot investigations and product development. Results of these pilot investigations have shown the device to be more comfortable when compared with standard acrylic instruments. The soft-solid instrument was shown to accommodate the pivotal action of the jaw in that most wearers reported that the hearing aid, once seated, did not need repositioning over the course of the day. In other words, this soft-solid material was found to eliminate the migration of the hearing aid from the ear due to jaw movement. Hearing instrument users with a history of excessive feedback reported a reduction in feedback when using the soft-solid devices. For some wearers, feedback was entirely eliminated when using a soft-solid device. Finally, pilot investigations found the soft-solid instrument appropriate for patients with bulbous, tortuous, or surgically altered ear canals.

In addition to the improvements in fit and comfort, the soft-solid instruments were found to provide more overall gain in the ear canal than acrylic devices due to the reduction of feedback. In other words, patients were able to increase the gain of the hearing aid (via the volume control) more in the soft-solid devices before reaching the point of feedback. This increased utility of gain may allow for a greater fitting range of completely-in-the-canal hearing instruments. Finally, many patients reported improved sound quality and "distinctness of sounds" when comparing the soft-solid devices to acrylic devices. This may be attributed to the finding in the pilot investigations that the soft-solid devices produced greater mid-frequency gain in the real ear compared to an acrylic device with the same 2 cc data.

These preliminary finding of the pilot investigation warrant a controlled clinical trial of the soft-solid hearing device.

The present invention, because of its soft nature, will not exert pressure on the bony portion of the external ear canal making it easily insertable beyond the second anatomical bend. This deeper insertion reduces residual volume between the proximal tip of the instrument and the tympanic membrane. Because sound pressure increases as residual volume decreases, more power is perceived without a corresponding increase in the gain of the instrument.

The present invention, because of its soft nature, will better accommodate anatomic aberrations such as tortuous ear canals, bulbous ear canals, stenotic ear canals, and iatrogenically altered ear canals.

The present invention, because of its solid nature, will protect the embedded electronic components.

The present invention, because of its solid nature, will eliminate the internal air conducted feedback pathway from the receiver to the microphone.

The present invention, because of its solid nature, will eliminate the need to suspend the receiver by tube-mounting, thereby preventing displacement of the receiver within the hearing instrument and eliminating the concomitant Helmholz resonation.

The present invention, because of its soft-solid nature, can be formulated in such a way as that the elastomer can be blended with conductive particles, such as gold dust or ferrite dust, to form a static shield protecting the circuitry from Radio Frequency Interference (RFI), Global System for Mobile Communication (GSM), and Electromagnetic Interference (EMI).

The present invention, because of its solid nature, can support the receiver and associated tubing. Because of its soft nature, the invention is compressible. Therefore, by compressing the tip of the instrument, cerumen can be extruded away from the receiver and out of the receiver port.

The present invention, because of its soft proximal tip, has a less reflective external surface than the traditional acrylic tip, thereby reducing intermodulation and reverberation.

The present invention, because of its solid nature, has no internal reflective surfaces, thereby eliminating internal reflection and reverberation.

The present invention, preferably comprising an elastomer blend at the very low end of the shore A scale (preferably ranging from 0–17 Durometer), will provide a platform for the manufacture of a series of universal, non-custom, soft-solid devices.

The present invention, because of its solid nature, provides for precise, uniform vent diameters, thereby providing predictable electro-acoustic responses.

The present invention, when incorporating a soft faceplate, results in a completely soft hearing instrument.

The present invention, because it is processed by casting a female cavity from the impression, eliminates buffing, waxing, and other means of impression modification inherent to current shell manufacturing procedures. By streamlining the assembly procedure, the present invention is more easy to produce and—consequently—less expensive to manufacture than the traditional hard, hollow acrylic shell.

The present invention includes the soft-solid body described herein, even when it is not filled with electronic components.

The present invention will accommodate additional personal communication devices such as telephones, pagers, memo-recorders, and two-way communication devices, instead of or in addition to hearing aids. In some cases (especially when a hearing aid is not included) it will be desirable to not make a good acoustic seal so that the person using the personal communication devices can also easily hear what is around him.

The present invention, because of its solid nature, can accommodate a bladder mounted in the center which can be filled with a soft material while positioned within the human ear canal. While the device remains in the ear canal, the soft center can be allowed to cure to a hardness less than 35 Durometer Hardness, Shore A. Also, the bladder could be used to vary the amount of occlusion by varying the amount of gel present in the bladder—in such a case, there could be a valve to allow filling and evacuation of the bladder. A hypodermic syringe, for example, could be used to fill and evacuate the bladder. The soft material can comprise a gel elastomer or petroleum jelly, for example.

The present invention can be produced with a sufficiently low Durometer (e.g., 3–17) so as to allow sleeping with the instrument in place.

The current preferred embodiment of the invention eliminates the need for modifications of ear impressions, generally accomplished through altering the shape of the impression and waxing the altered impression. Hence, a more direct method of casting is achieved, yielding greater accuracy of topographical detail of the ear canal in terms of dimensional and geometric characteristics.

The preferred embodiment utilizes a material that is a blended silicone that accepts bonding to plastic by adhesives. Other embodiments of the invention may utilize rubbers, elastomers, and other rubber-like materials including neoprene, silicone, vinyl, butyl and soft plastics.

Preferably, the body occupies at least 70% of the volume of the hearing device not occupied by the electronic hearing circuit. More preferably, the body occupies at least 80% of the volume of the hearing device not occupied by the electronic hearing circuit. Even more preferably, the body occupies at least 90% of the volume of the hearing device not occupied by the electronic hearing circuit. Most preferably, the body occupies at least 99% of the volume of the hearing device not occupied by the electronic hearing circuit.

The outer surface of the body of the present invention is preferably non-absorbent and virtually impervious to cerumen.

BRIEF DESCRIPTION OF THE SEVERAL VIEWS OF THE DRAWINGS

The manufacturing method according to the invention and the hearing instrument manufactured by this method is further described in the following detailed drawings, wherein:

FIG. 6 shows the device as described in FIG. 2 except with an iatrogenic variant demonstrating a post surgical ear canal;

FIG. 7 shows the device as described in FIG. 2 demonstrating ear canal configuration change and canal angle variance between the jaw open position and the jaw closed position.

FIG. 8 shows preferred embodiment of the invention including one embodiment of the wax chamber;

DETAILED DESCRIPTION OF THE INVENTION

Figure 1:
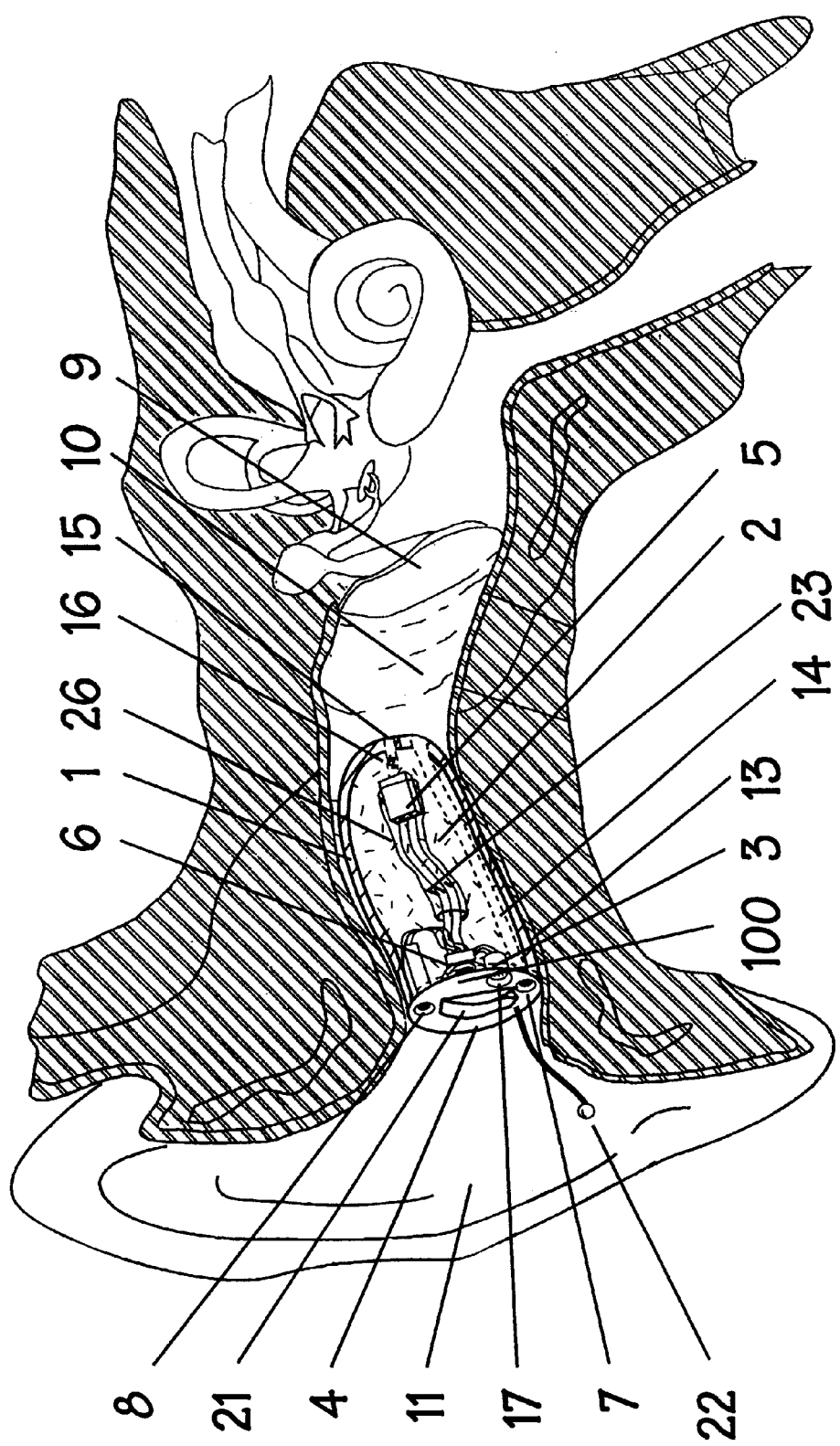
FIG. 1 shows the device of the preferred embodiment of the present invention in a typical human ear from a side perspective.

FIG. 1 shows one configuration of a complete device in the human ear from a side perspective. Outer layer 1 is a soft outer layer (such as a polydimethysilioxane layer of 35 Durometer hardness shore A, such as Dow Corning® MDX4-4210 (which is used in the current embodiment)). This outer layer 1 acts as a general surface skin that provides greater resistance to tearing and provides the stiffness for insertion. The outer layer 1 also provides resilience, durability, and abrasion resistance. A softer center 2 is preferably made of the same polydimethysilioxane except with functional groups and fillers (such as Intrinsic II (I300) and Functional Fluid (A313), and is preferably less than seventeen points Durometer hardness, shore A, such as Factor II Realistic (A-588). This soft center provides the wall pressure necessary to maintain the acoustic seal between the device 100 and the ear canal wall 13 from the sagittal plane of the aperture medially to the end of the device. Further, the composite of outer skin 1 and center 2 has elastomeric properties that allow the device to flex with jaw excursion, thereby eliminating the external acoustic loop between the receiver 5 and the microphone 8.

Layers 1 and 2 can be of equal stiffness and can be only a single homogeneous filling composing the center and outer boundaries and everything in between. Thus, the device body could be homogenous (the outer layer could be eliminated). It is believed that the flexibility of viewing these as separate layers allows for the mixing and refining of different elastomeric characteristics.

In one embodiment, a ratio of elastomer, non-functional extenders and catalyst is used in layer 2 with the final hardness of layer 2, the center layer, being off the A scale, i.e. "0" A or an elastomer gel. The end result is a soft, gel filled device which is compliant and flows with pressure. This compliance serves to eliminate the pivoting of the device that results in displacement. The soft center also serves to eliminate the internal air conduction path between the receiver 5 and the microphone 8 innate to traditional hollow hearing aid shells. A bonding agent 3, such as Factor II silicone bonding enhancer (A-320), adheres the soft bodies of layer 1 and center 2 to the plastic faceplate of the device 4, such as the In'Tech® model 10A faceplate. A typical microphone 8 such as a Knowles® model TM 3546, and a typical acoustic receiver 5 such as a Knowles® model ES7653, are coupled to a typical amplifier 6 such an Etymotic Research model ER-47D K-Amp DSD programmable hybrid, and are populated with capacitors and other components. A typical programming socket 17 such as a Microtronic CS44, is coupled to the amplifier assembly, and serves as the interface between the hearing instrument and the programming unit.

Sound enters the microphone 8 and is transduced into an electrical signal then transmitted by a wire (such as a five strand, forty-four gauge wire) 23 to the amplifier 6. A wiring harness connecting the receiver 5 to the amplifier 6 with an optional but preferred S-shaped loop 26 (see FIG. 14) acting as a strain relief allows the two components to move away from each other and back again when the body of the instrument is being squeezed or flexed. When employing high gain and high output, the signal is conducted by wire to a capacitor 27 (see FIG. 13) mounted on board the receiver 5, in lieu of the customary location upon the amplifier substrate. This smooths the response curve by reducing the effect of any heterodyning interference due to the antenna effect of the longer receiver wires which are necessary to accommodate the strain relief loop 26. The signal is then transduced back to an acoustic signal by the receiver 5. The acoustic signal then enters a wax guard 15 including a preferably spherical cavity which extends to a preferably cylindrical tube. This cavity is loosely filled with an acoustic medium 16, usually lambs wool or foam, which acts as a wax protection system for the receiver 5, and further serves to smooth out the peaks of the acoustic response. Venting system 14 allows for pressure equalization during swallowing and reduces the low frequency sound spectrum. The vent system 14 can be molded in place using a silicone tube and removing it once the soft-solid hearing aid body has completely vulcanized. In a similar manner, the wax guard 15 can be molded by a tube and sphere which are withdrawn once the body of the device has cured. Both venting system 14 and wax guard 15 are optional depending on the hearing loss and the physical size and shape of the particular ear being fit.

Figure 2:
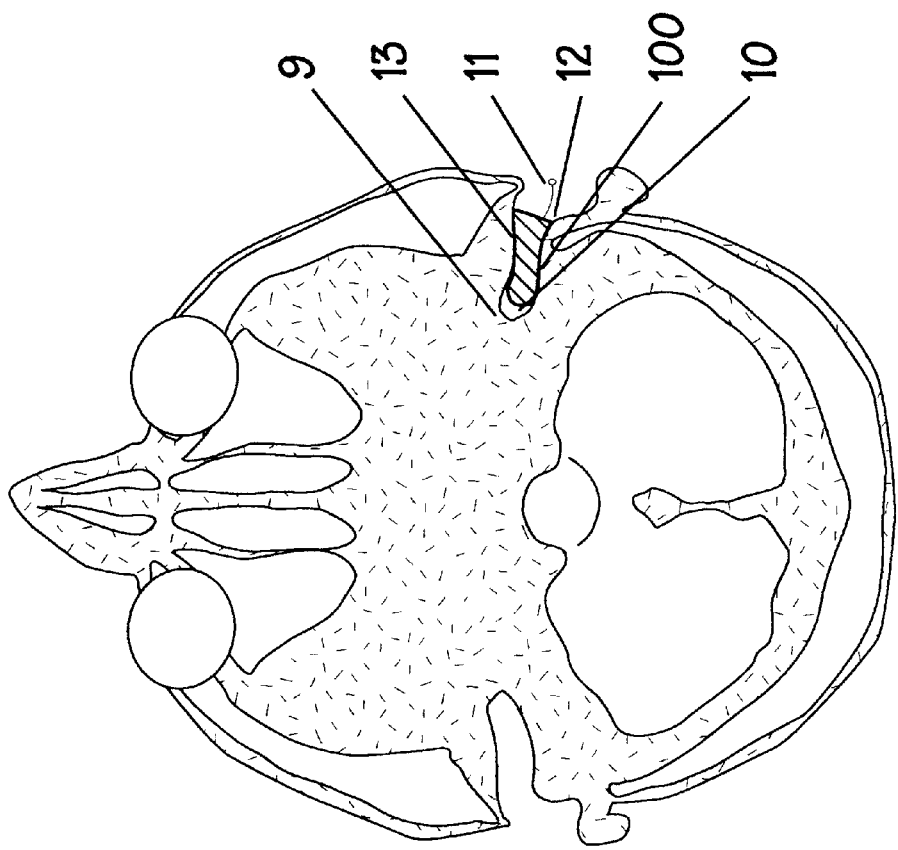
FIG. 2 shows the device in a graphically illustrated view of a typical human ear viewed superiorly.

FIG. 2 shows the device 100 in a graphic illustration of a typical human ear as viewed superiorly. The tympanic membrane 9 accepts the output of the soft-solid device 100 There is a snug and uniform acoustic seal between the canal wall 13 and the outer wall 1 of the device 100. This snug and uniform acoustic seal between the canal wall and the outer wall of the device is maintained during jaw motion and head movement.

Figure 3:
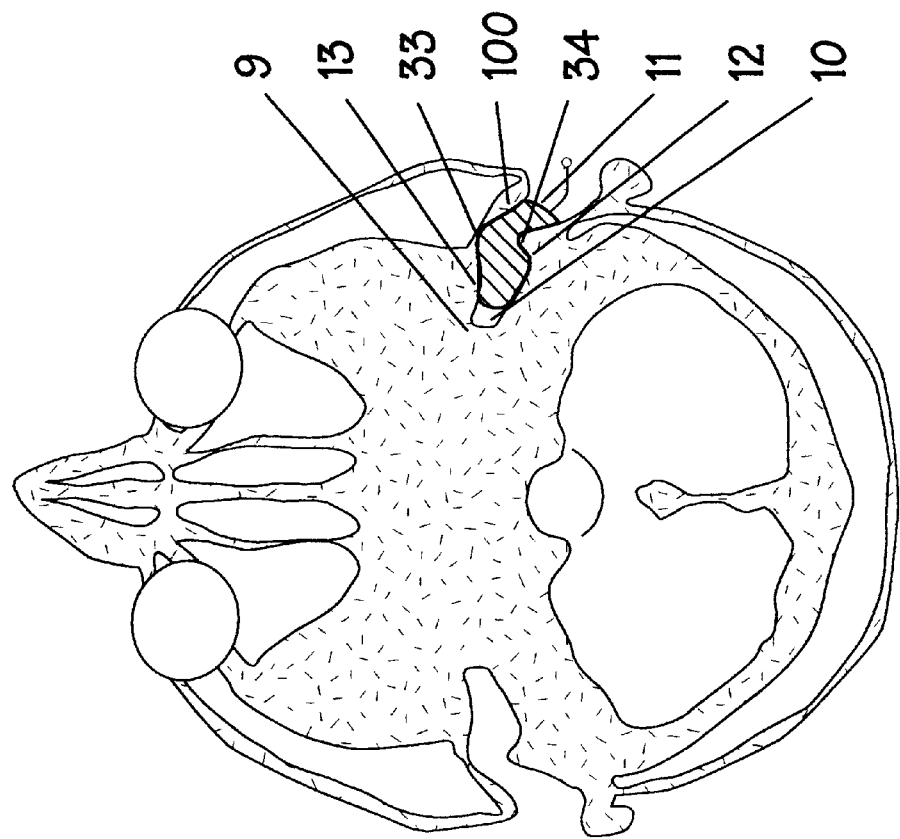
FIG. 3 shows the device as described in FIG. 2 except with an anatomic variant defined as a bulbous ear canal.

FIG. 3 shows the device 100 as described in FIG. 2 except with an anatomic variant defined as a bulbous ear canal. The opening to the bulbous external ear canal is geometric narrowed by the anterior 33 and the posterior 34 ear canal surfaces at the first directional bend. The device 100 compresses as it is inserted through the narrowing with the soft solid device layers 1 and 2 returning to their normal state once the device 100 is in its final seated position.

Figure 4:
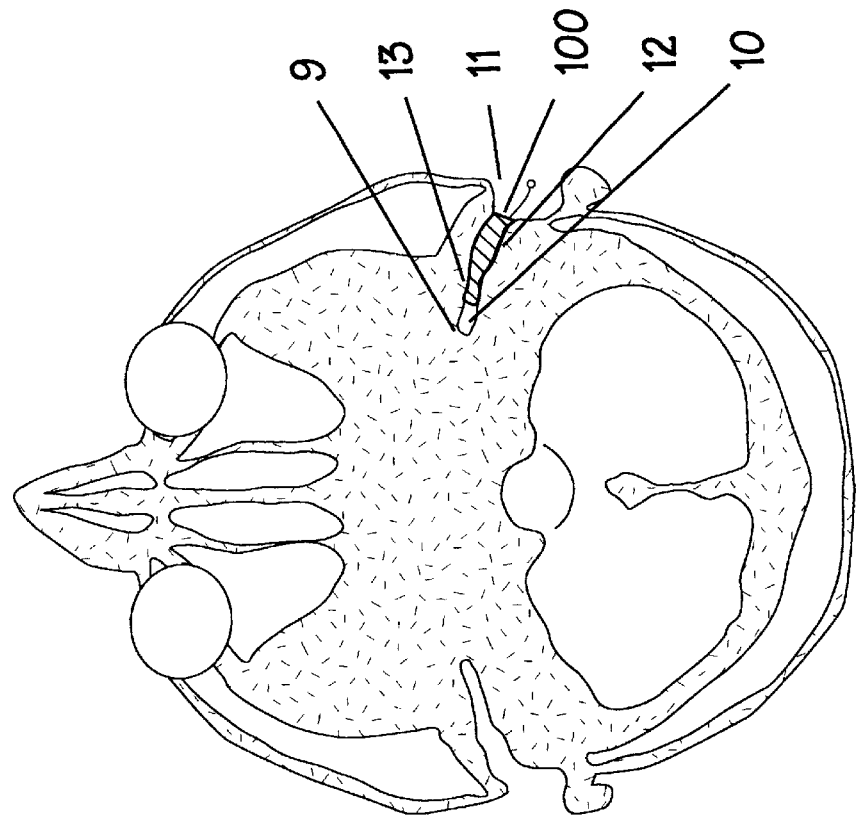
FIG. 4 shows the device as described in FIG. 2 except with an anatomic variant defined as a stenotic ear canal.

FIG. 4 shows the device 100 as described in FIG. 2 except with an anatomic variant defined as a stenotic ear canal. The ear canal progressively narrows medially. Because of the solid-soft nature of the device, the need to build up the medial tip of the instrument to suspend the receiver is eliminated.

Figure 5:
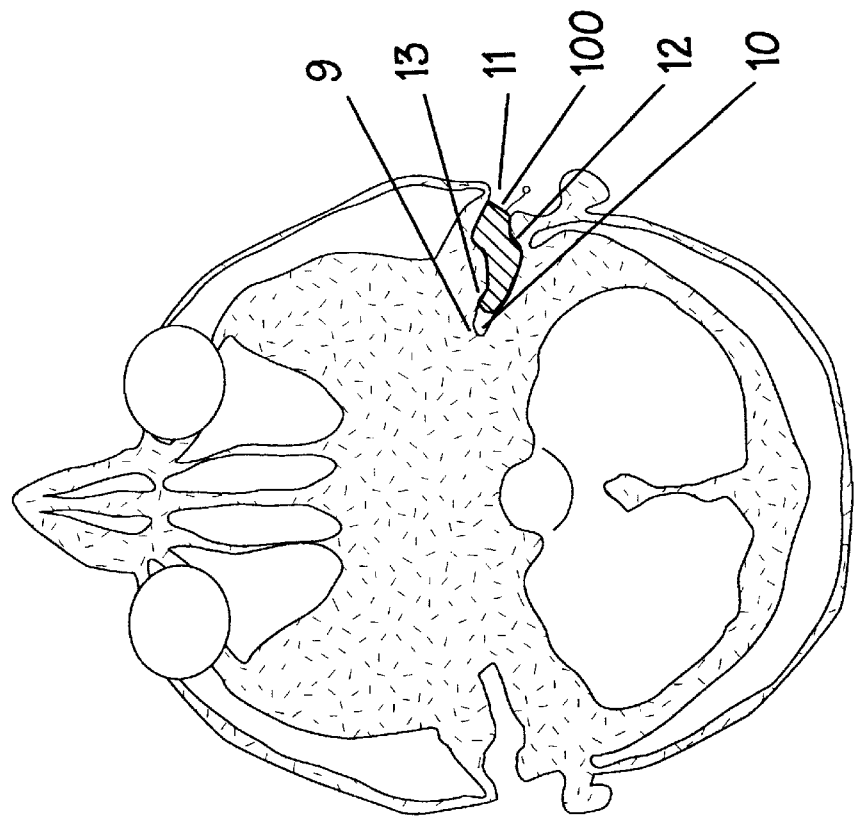
FIG. 5 shows the device as described in FIG. 2 except with an anatomic variant defined as a tortuous ear canal.

FIG. 5 shows the device as described in FIG. 2 except with an anatomic variant defined as a tortuous ear canal. The ear canal has a sharp turn between the first and second bends, and turns again beyond the second bend. Because of the soft nature of the instrument, the device 100 is able to flex around the canal angles, presenting the desired receiver angle toward the tympanic membrane 9.

FIG. 6 shows the device as described in FIG. 2 except with an iatrogenic variant demonstrating a post surgical ear canal. The ear canal has been surgically widened, while the rising plane of the ear canal has remained. Because of the firm acoustic seal between the outer skin of the instrument 100 and the external ear canal wall 13, the instrument will resist migration out of the ear canal in response to jaw motion or head movement. Further, the softness of the product reduces the pressure on the facial nerve usually rerouted as part of normal surgical protocol.

FIG. 7 shows the device as described in FIG. 2 demonstrating ear canal volume change and canal angle variance between the jaw-open position 37 and the jaw-closed position 38.

FIG. 8 shows the preferred embodiment of the present invention including the preferred embodiment of the wax chamber 15. Receiver 5 is mounted in the soft-solid 2 inner layer. A cavity is formed by the extreme distal end at the receiver's port medially outward, which is filled with acoustic media 16 to serve as a wax barrier and an acoustic damper which will smooth the acoustic response of the receiver.

Figure 9:
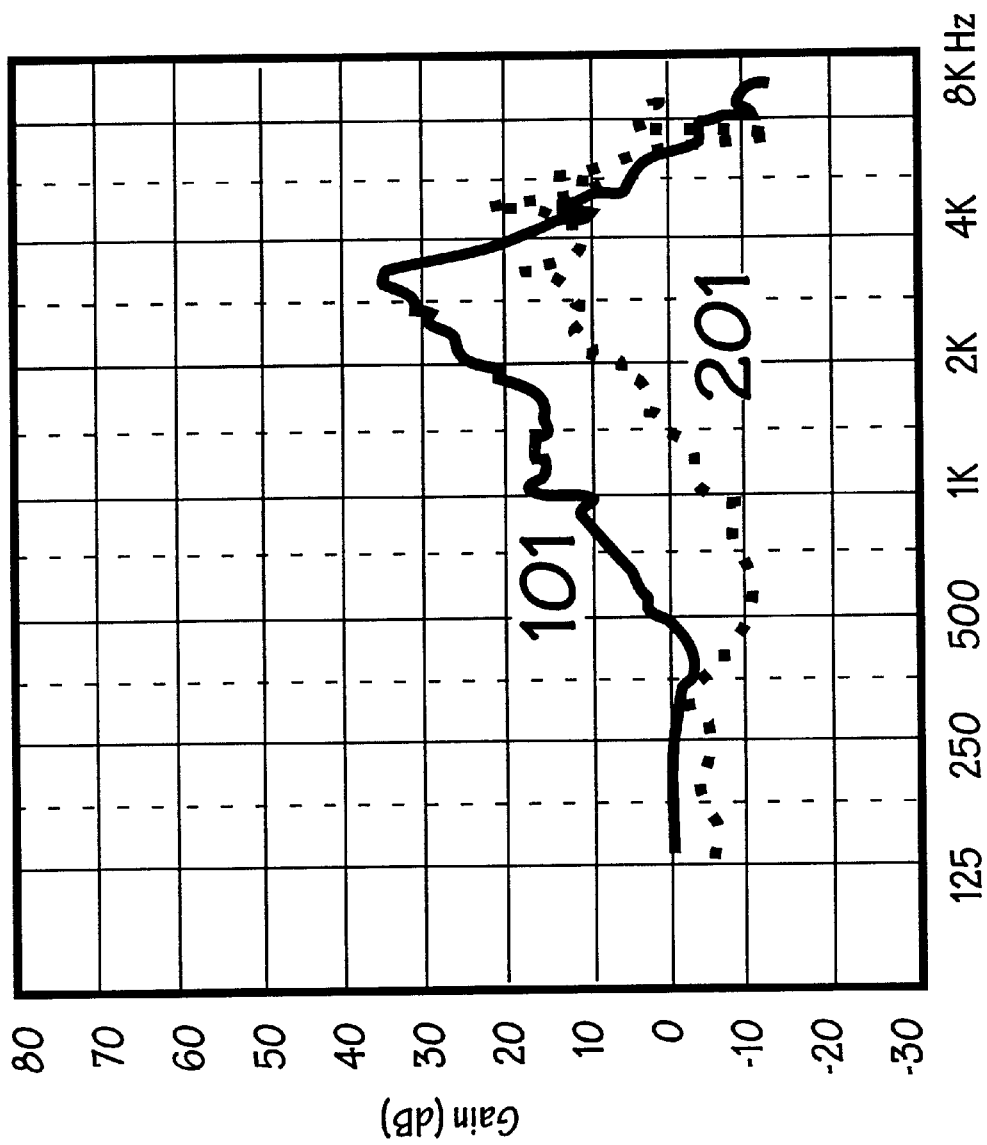
FIG. 9 shows an acoustic illustration of a typical response.

FIG. 9 shows a typical real ear acoustic response of the device 100 before the onset of feedback. Curve 101 represents the soft solid device and curve 201 represents a hard, hollow acrylic device of identical, electro-acoustic design. Curve 101 reveals greater acoustic gain and sound pressure levels before feedback.

Figure 10:
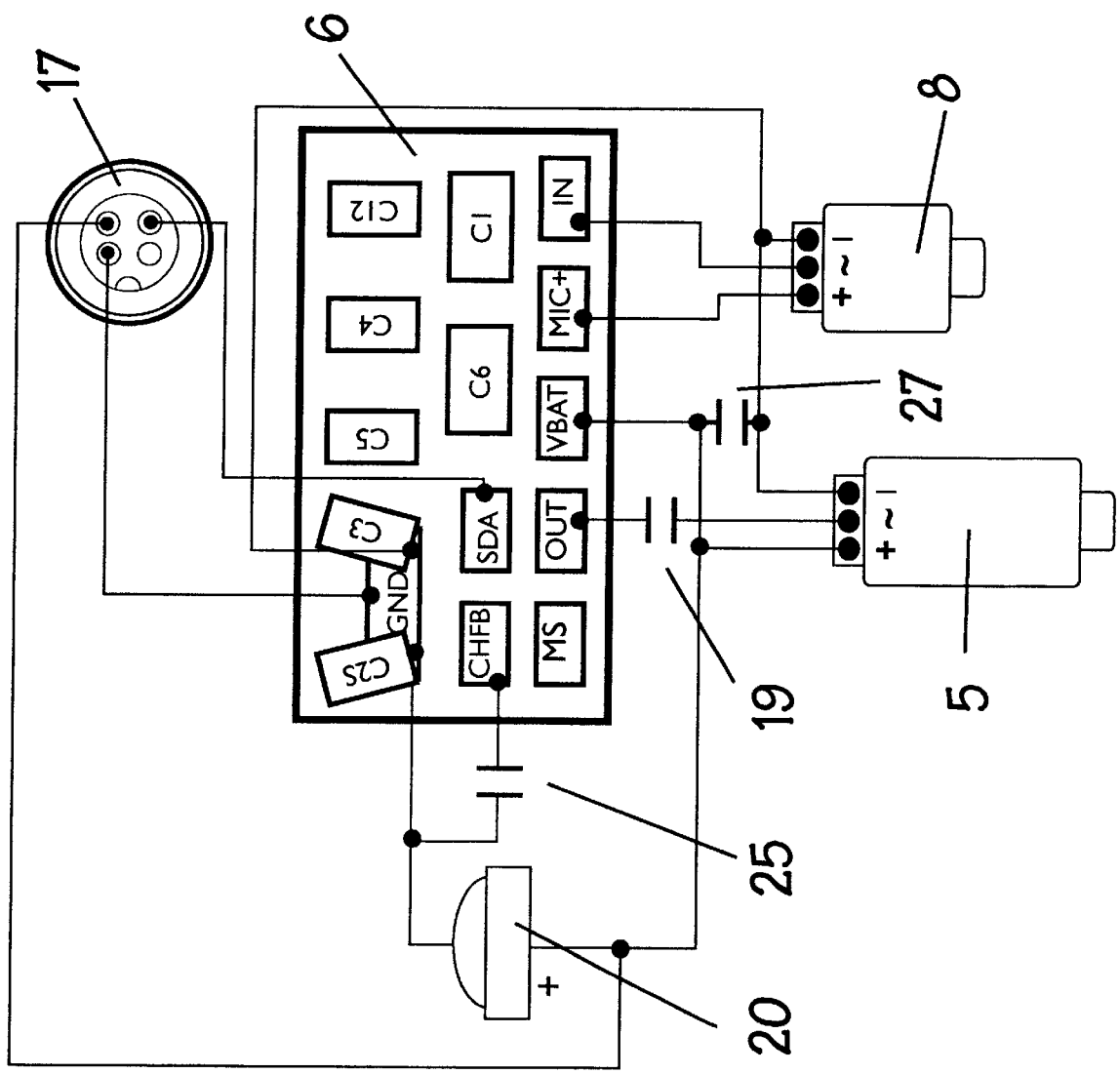
FIGS. 10 and 11 show two typical hearing aid designs being currently produced.

FIG. 10 shows a typical single channel programmable K-Amp 6 hearing aid design being currently produced. Incoming sound enters the microphone 8 where it is transduced to an electrical signal. It then enters the amplifier 6 for processing and amplification, then enters the CHFB capacitor 25 for high frequency signal boost. It then returns to the amplifier and then to the output capacitor 19 which isolates the DC and AC components. The trimming capacitor 27 then filters the signal of distortion caused by heterodyning or other radio frequency interference. The signal is then transduced back into sound in the receiver 5. The programmable adjustments to the microprocessor are addressed through the programming socket 17 and then by the programmer of choice.

Figure 11:
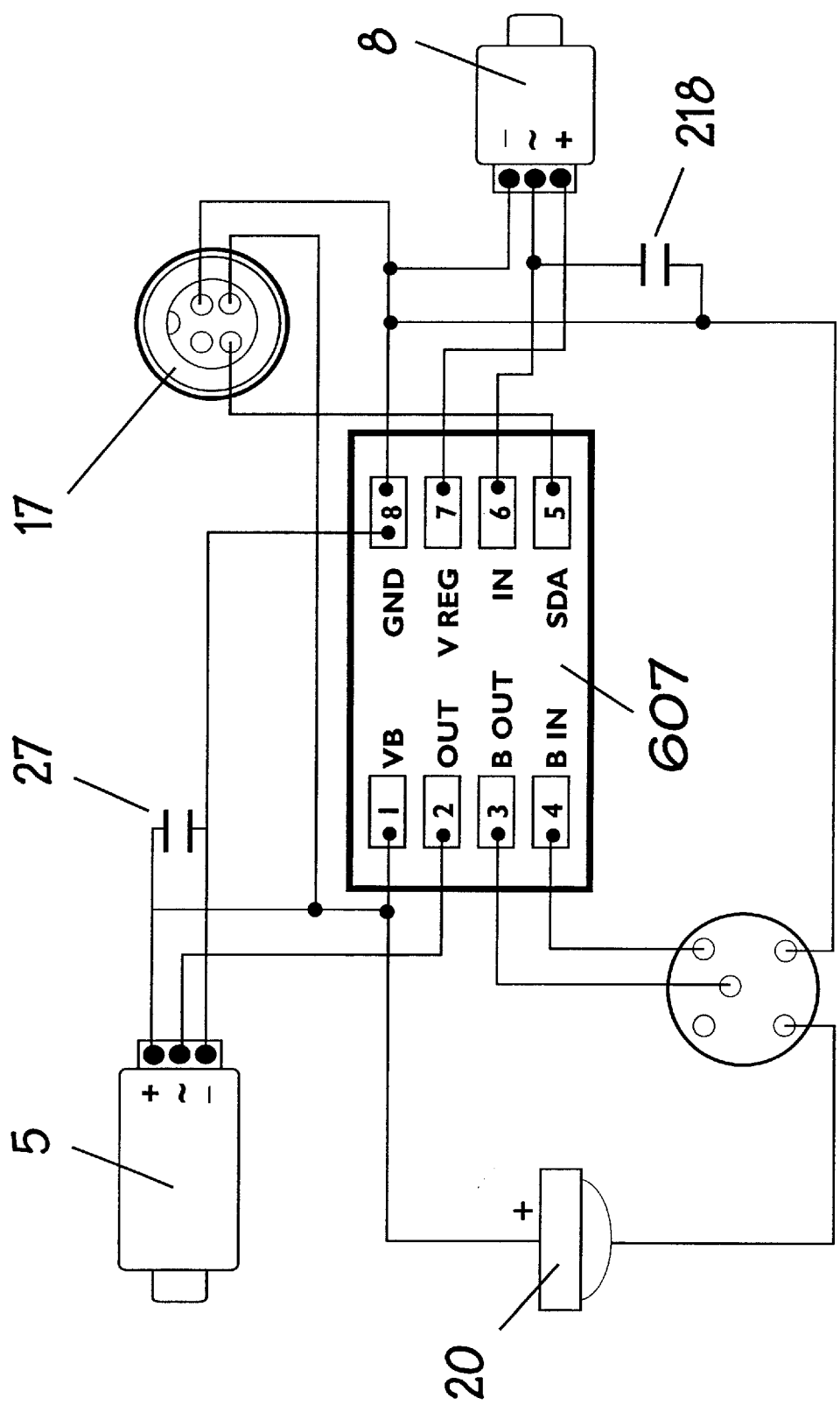

FIG. 11 shows a typical dual channel programmable DEQII hearing design being currently produced. It should be noted that many hearing aid circuits and other types of circuits could be housed in this soft solid embodiment. Examples include 100% digital circuits, such as the Widex Senso, the Oticon Digifocus, the Philips Open-platform digital, the Siemens Prisma, and others to come, and mass communication devices such as: pagers, beepers, cellular phones, digital phones, and composite devices of the above which are currently in development.

Figure 12:
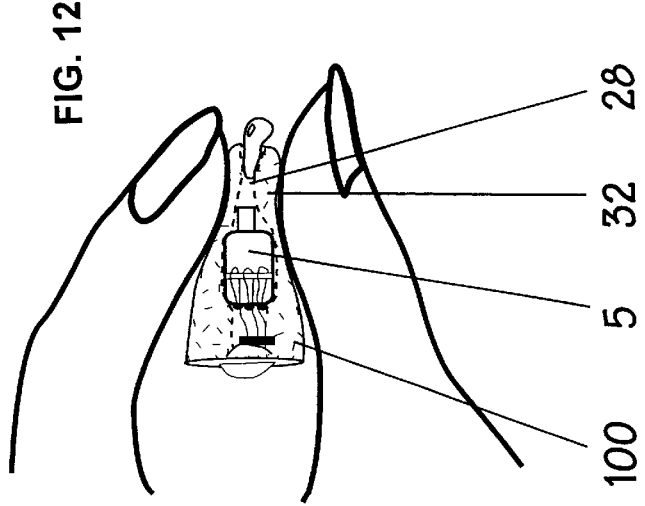
FIG. 12 shows an alternative tubed wax guard system.

FIG. 12 shows an alternative, "tubed wax guard" system 28. The receiver 5 is mounted with silicone tubing 32 of sufficient length (4–8 mm). Visual inspection, since the product is a clear translucent elastomer, reveals the presence of ear wax which is ejected by pinching the device 100 between the index finger and the thumb. Positive pressure is formed by the closed tube to the receiver and relieved to the outside world.

Figure 13:
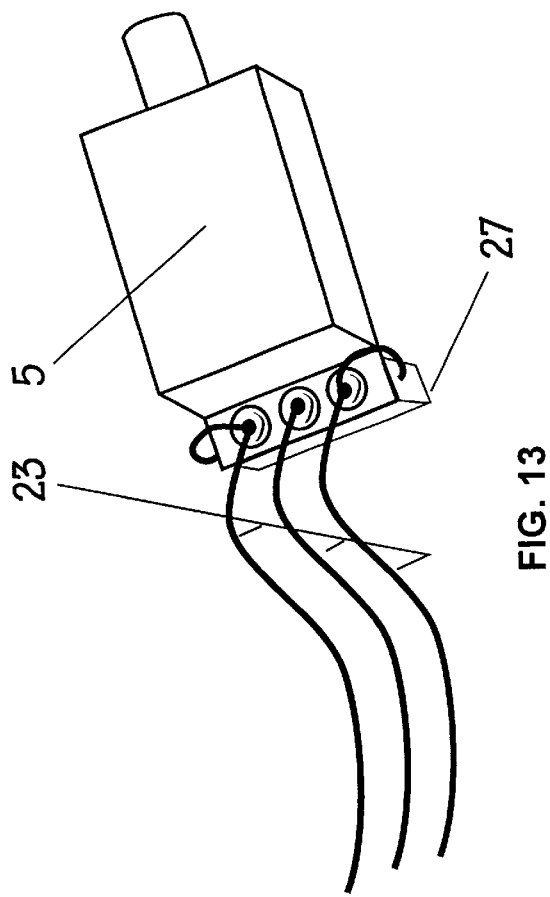
FIG. 13 shows an alternative capacitor location to reduce heterodyning of the amplified signal.

FIG. 13 shows an alternative capacitor location to reduce heterodyning of the amplified signal. The bunching and coiling of the receiver 5 wires in the "S" shaped bundle 26 cause an antenna effect commonly referred to as heterodyning; this is represented as spikes in the acoustic response curve. Mounting the trimming capacitor 27 at the receiver terminal board filters this effect.

Figure 14:
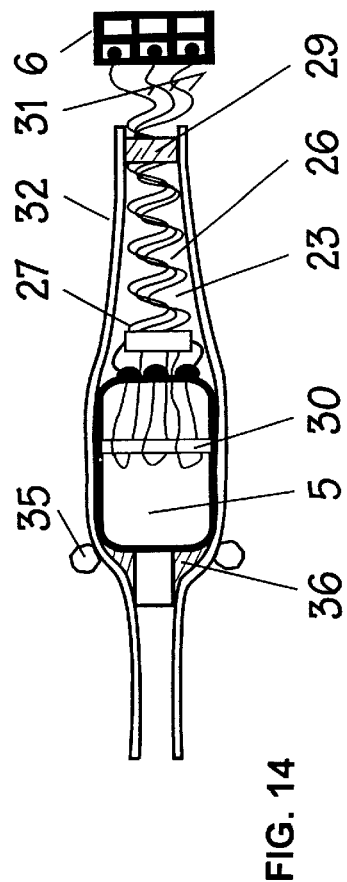
FIG. 14 shows an embodiment of the strain relief system of the present invention.

FIG. 14 shows the preferred embodiment for the strain relief system 26. The dynamic nature of electronic components embedded in a soft elastomer create the need for hard wiring to be connected to the components and yet maintain the ability to allow the components to move with flexing of the device 100. The receiver 5 is mounted in tubing 32 with the anti-heterodyning capacitor 27 on board the receiver box. The wires 23 are soldered in place and routed to a compression strain relief 30 at the lateral end of the receiver. The wires then enter the tubing and are bunched into an S-shaped bundle 26 forming a compressible and telescopic harness which will accommodate the tensile force, compression force, axial torque, and radial torque exerted by the device 100. Plug 29 is used to maintain the air cavity formed between the plug and the receiver lateral end. Receiver 5 is sealed at the extreme distal end at its port 36 to prevent acoustic leakage and cerumen penetration. The wires 23 are then anchored by a tacked strain relief 31 and then connected to the solder pads of the amplifier 6

Figure 17:
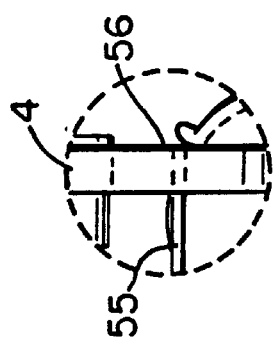
FIGS. 15–17 show a strain relief and receiver positioning system of the preferred embodiment of the present invention.
Figure 16:
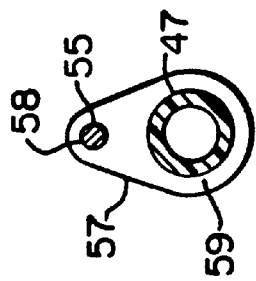
Figure 15:
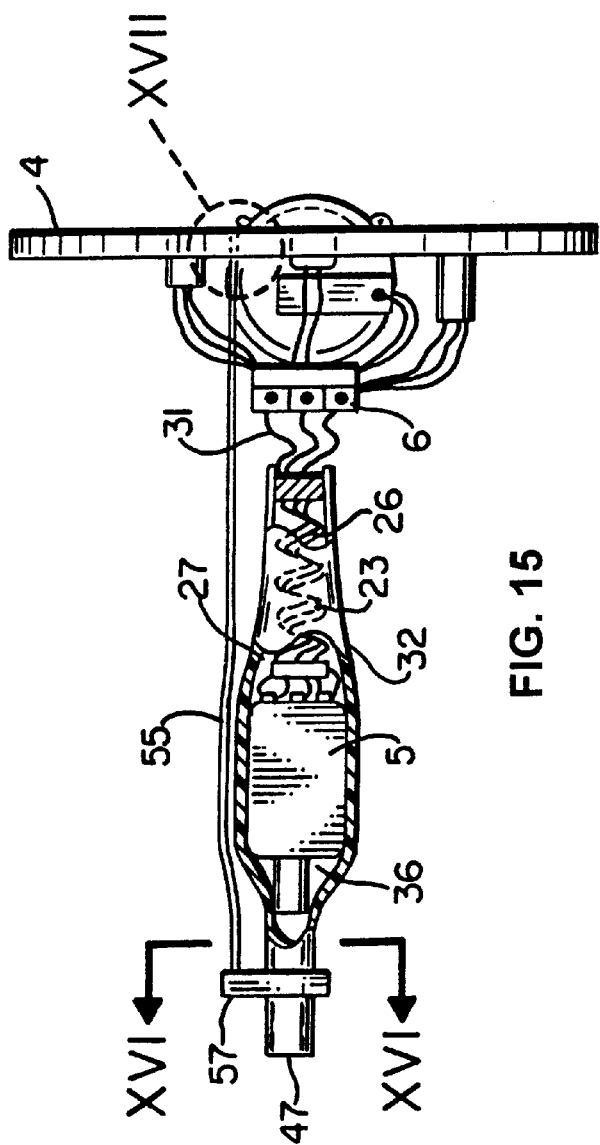

FIGS. 15–17 show a strain relief and receiver positioning system of the preferred embodiment of the present invention. The strain relief and receiver positioning system includes a monofilament cantilever 55 can be used to carry tension so that tension is not transmitted to the wiring harness including wire loops 26. In FIGS. 15, 16, and 17 the cantilever 55 is anchored to plate 4 at opening 56. A fastener 57 affixes to receiver tube 47 at large opening 59. Monofilament cantilever 55 attaches to fastener 57 at smaller diameter opening 58. The components shown in FIG. 15 can be encapsulated with soft solid material as shown in FIG. 1.

The monofilament cantilever 55 provides longitudinal stability to the body. It minimizes longitudinal displacement (stretching as well as compression) and thus acts as a longitudinal stabilizer (a longitudinal load carrying member).

Instead of using fastener 57 and monofilament cantilever 55, one could use a double lumen tube to act as receiver tube 47 and as a vent 14 which will also act as strain relief.

TYPICAL SOFT-SOLID MATERIALS:

Elastomers: Dow Corning® MDX4-4210 Base and Dow Corning® MDX4-4210 Curing Agent

Acetone

Preferred elastomers: Factor II Realistic II Polydimethysiloxane with functional groups and fillers) (A-588, A-588T, or A-588V)

Factor II Silicone Primer (A-304)

Factor II Silicone Bonding Enhancer (A-320)

Audacryl RTC Methacrylate Monomer Mixture

Audacryl RTC Poly Ethyl Methacrylate (clear)

TYPICAL HEARING AID CIRCUIT COMPONENTS:

Tansitor® 2.2 capacitor

Tansitor® 0.047 capacitor

RTI® 10A hard battery boot

Insulated stranded wire silicone tubing

TYPICAL EARMOLD PREPARATION:

The following procedure is a description of an alternative, soft-solid body manufactured without the outer skin. The hardness of the soft-solid body is preferably 5–55 Durometer, Shore A, more preferably 5–35 Durometer, Shore A, and most preferably 7–20 Durometer, Shore A.

A. Preparation of the Impression and Construction of the Acrylic Cast

The preferred impression should be of a material such as silicone, since the dimensional stability and elastic memory are crucial to a faithful reproduction of the ear cavity. The use of polymethyl methacrylate is not recommended because of poor dimensional stability (notably, shrinking after 48 hours). The canal length of the impression should extend at least 3 mm past the second bend of the external auditory canal. The open mouth ear impression technique is recommended.

The impression is sized to the desired length, consistent with deep insertion technology. Topographic details of the impression are maintained.

The impression is sprayed with silicone mold release.

A female cast is formed by dipping the impression in uncured acrylic. The cast should have a wall thickness of 2 mm.

The acrylic cast is thermally cured in water or exposed to ultraviolet (UV) light for a two-minute period. The acrylic cast is clear to allow for easy observation of the electronic components during the molding process.

The impression is then removed from the acrylic cast. The lateral face of the acrylic cast is decked down to meet the requirements for the desired hearing instrument style (e.g., CIC, ITE).

B. Preparation of the Electronics

Electronics are assembled on the plate per standard hearing instrument procedure with the following differences:

A full hard battery boot should be used, and should be sealed completely.

Components should not come into contact with the acrylic investment.

The microphone port is drilled into the faceplate, and the microphone is surface mounted. The microphone and looped microphone wiring are sheathed in silicone tubing.

A wiring harness connecting the receiver to the amplifier with an S-shaped loop acts as a dynamic strain relief system. This protects the wire elements and the solder pads on the circuit board and on the receiver during flexion or compression of the instrument.

C. Preparation of the Faceplate

The faceplate is prepared with a coating of acetone, and is set aside to dry.

Once the acetone coating has dried, the primer is applied and the faceplate is set aside to dry for a thirty minute period.

Following that, a coating of the bonding enhancer is applied and is set aside for a thirty minute drying period.

D. Closing Procedure

The receiver port, the vent port, and a filling port are drilled into the acrylic cast. The inside of the acrylic cast is thoroughly cleared of debris.

The receiver tube and the vent tube are positioned in the cast.

The electronics are positioned into the cast. Thee faceplate is mounted onto the cast, and is cycobonded to the cast.

E. Filling Procedure

The soft elastomer material (preferably Factor II Realistic II Polydimethysiloxane with functional groups and fillers, A-588, A-588T, or A-588V) is injected through the filling port via syringe. Any existing air bubbles should be eliminated (e.g., by pulling a vacuum or adding a thixotropic agent such as Thixo available from Factor II).

The microphone and receiver tubes are sealed with elastomer plugs to prevent water from infiltrating the transducers.

The elastomer in the filled shell is thermally cured in water maintained at 120 degrees Fahrenheit (water is sometime preferred because of the better heat transfer characteristics of water, though air could be used as there is less chance of damaging the electronic components if air is used to thermally cure the elastomer). The temperature may be increased to quicken the curing time, but should preferably not exceed 140 degrees Fahrenheit.

F. Finishing Procedure

The acrylic cast is scored with a metal bit. Snips are used to clip along the scored areas and to remove the cast from the instrument.

Once the cast has been removed, a heated ruby bit is used to finish the seam between the body of the body and the faceplate of the instrument.

The soft-solid hearing instrument of the present invention has a soft-solid nature which provides an environment for the electronic circuit that will improve transducer performance, improve transducer longevity, and will be more resistant to vibration, force, and shock, as compared to hollow hearing aids. Because of its soft nature, it will provide greater comfort, will resist migration out of the ear canal, and will remain acoustically sealed with jaw excursion. Because of its soft nature, it will allow for the full utilization of advanced electronic performance of which high fidelity programmable and digital designs are capable.

Because of its soft nature and because its superior acoustic seal, it reduces or eliminates unwanted acoustic feedback. Because of its soft nature, it will be easily insertable, will accommodate anatomical aberrations, and will—because of its capability of being deeply inserted beyond the second anatomical bend—provide increased perceived power. Because of its solid nature, it will have no internal surfaces, thereby eliminating internal reflection and reverberation, eliminating the internal feedback path between the receiver and the microphone.

Coloring of the elastomer is possible using two methods. The first method is intrinsic, under the surface layer. The second method is extrinsic, on the surface layer. The methods can be done separately or in conjunction with one another.

The preferred method is intrinsic coloring, whereby a special dye is mixed thoroughly into the uncured material in very small ratios (e.g., 1 drop per 10 grams). Once the mixture is completed, the material is cured in the same way as would be the uncolored material. An alternative method is extrinsic coloring, whereby an extrinsic tri fluid solvent is applied to the surface of the cured material, causing the pores of the material to open. At that point, dye is brushed onto the surface of the material. As the solvent dries, the pores of the material close, and the dye is enveloped.

Service of the electronic components is accomplished by making an incision in outer layer 1 and center layer 2 until the damaged component is exposed for repair or replacement. Material bonding approach (also addresses repair issue): the preferred method involves cleaning the damaged site on the instrument with alcohol and allowing it to dry. A thin coat of bonding enhancer (A-320) is applied to the site, which is then allowed to dry for thirty minutes. Once the bond enhancer has dried, a layer of soft-solid material is applied. The instrument is then cured for thirty minutes in an oven which has been preheated to 60 degrees C. If necessary, the repaired site can be sculpted to conform to the original shape of the instrument.

An alternative method involves applying a layer of acetic acid based elastomer onto the damaged site on the instrument. That elastomer serves to open the pores of the material, bonding the materials. The instrument is then cured for thirty minutes in an oven which has been preheated to 60 degrees C.

Parts List:

The following is a list of parts and materials suitable for use in the present invention:

1 soft-solid outer skin (optional)
2 soft-solid inner body
3 bonding agent
4 faceplate (such as an In'Tech® 10A Faceplate)
5 receiver (such as a Knowles® ES7653 receiver)
6 amplifier (such as an Etymotic Research ER-42D K-Amp®/DSD programmable hybrid)
7 vent hole in faceplate 4
8 microphone (such as a Knowles® TM3546 microphone)
9 TM
10 cavity
11 concha
12 sagittal plain or aperture of ear canal
13 external ear canal wall
14 vent in hearing aid
15 wax guard
16 acoustic media (such as lambs wool or foam) in wax guard
17 programming socket (such as a Microtronic CS44 socket)
18 input decoupling capacitor
19 output decoupling capacitor
20 battery 21 battery door (such as an In'Tech® 10A Battery Door)
22 extraction cord
23 44 gauge 5 strand wire
24 volume control
25 CHFB capacitor
26 "S" loop strain relief
27 Trimming cap for heterodyning
28 alternate wax guard system
29 Adhesive plug
30 Compression strain wire relief
31 Tacked strain wire relief
32 standard silicone receiver tubing.
33 Anterior external ear canal wall
34 Posterior external ear canal wall
35 Centering nubbins
36 Receiver silicone seal
37 Open-jaw position
38 Closed-jaw position
47 receiver tube
55 monofilament cantilever
56 opening in plate 4
57 fastener
58 smaller diameter opening in fastener 57
59 larger diameter opening in fastener 57
100 Soft-solid hearing aid of the preferred embodiment of the present invention The body could be homogeneous (the outer layer 1 could be left out). Any suitable type of electronic schematic could be used instead of the schematic shown in FIG. 11.

All measurements disclosed herein are at standard temperature and pressure, at sea level on Earth, unless indicated otherwise. All materials used or intended to be used in a human being are bio-compatible, unless indicated otherwise.

The foregoing embodiments are presented by way of example only; the scope of the present invention is to be limited only by the following claims.

What is claimed is:

1. An ear-worn hearing device, the device comprising:
   (a) a hearing device body sized and shaped to generally fit into a human ear canal; and
   (b) an electronic hearing circuit that includes an amplifier, a microphone and a receiver assembly, said receiver assembly including a receiver and a receiver-tube at least a portion of said receiver assembly being embedded in the body, wherein: the body is made of a soft-solid elastomer and the body has a Durometer Hardness, Shore A, of less than 40 points.

2. A device as in claim 1, wherein the body includes an outer skin portion and an inner filler portion, and at least 90% of the body has a Durometer Hardness, Shore A, of less than 25 points and comprises the inner filler portion.

3. A device as in claim 1, wherein the body includes an outer skin portion and an inner filler portion, and at least 80% of the body has a Durometer Hardness, Shore A, of less than 35 points and comprises the inner filler portion.

4. A device as in claim 1, wherein the body includes an outer skin portion and an inner filler portion, and the inner filler portion is gel elastomer filled and has a Durometer Hardness, Shore A, of less than 35 points.

5. The device of claim 1, wherein the body occupies at least 70% of the volume of the hearing device not occupied by the electronic hearing circuit.

6. The device of claim 1, wherein the body occupies at least 80% of the volume of the hearing device not occupied by the electronic hearing circuit.

7. The device of claim 1, wherein the body occupies at least 90% of the volume of the hearing device not occupied by the electronic hearing circuit.

8. The device of claim 1, wherein the body occupies at least 99% of the volume of the hearing device not occupied by the electronic hearing circuit.

9. The device of claim 1, wherein the body is non-absorbent and substantially impervious to cerumen.

10. The device of claim 1, wherein the body shields, by means of encapsulation, the electronic hearing circuit from the hostile environment of the ear which usually causes corrosion of exposed connections.

11. The device in claim 1, wherein the device is a hearing aid having a receiver, a receiver port, and a medial end, and the receiver is recessed from the medial end of the instrument, thereby allowing cerumen to be extruded from the receiver port when pressure is exerted between the receiver and the medial end of the device.

12. The device in claim 1, wherein the body comprises a blend of elastomer and conductive particles to provide static shield protecting the circuitry from RFI, GSM, and EMI.

13. The device in claim 1, wherein the electronic hearing circuit includes a receiver, an amplifier, and a wiring harness connecting the receiver to the amplifier with an S-shaped loop.

14. The device in claim 1, wherein the electronic hearing circuit includes transducers and the body, because of its soft-solid nature, provides shock absorption for the transducers.

15. The device in claim 1, cast from a standardized impression of the ear, or from several selected sizes of the ear, so as to provide a platform to manufacture a series of non-custom, soft-solid devices.

16. The device in claim 1, cast from sufficiently low Durometer material so as to allow the device to be worn by the user while sleeping.

17. The device in claim 1, wherein the electronic hearing circuit includes hearing aid circuitry.

18. The device in claim 1, wherein the device is a completely-in-the-canal device.

19. The device in claim 1, wherein the body is custom molded.

20. A device as in claim 1, wherein at least 90% of the body has a Durometer Hardness, Shore A, of less than 25 points.

21. A device as in claim 1, wherein at least 80% of the body has a Durometer Hardness, Shore A, of less than 35 points.

22. A device as in claim 1, wherein the body is gel elastomer and has a Durometer Hardness, Shore A, of less than 35 points.

23. A device as in claim 1, wherein the body comprises a gel and has a Durometer Hardness, Shore A, of less than 35 points.

24. The hearing device of claim 1 wherein the elastomer is a bondable silicone.

25. The hearing device of claim 1 wherein the elastomer is Factor II A588.

26. The hearing device of claim 1 wherein the elastomer is Factor II A588T.

27. The hearing device of claim 1 wherein the elastomer is Factor II A588U.

28. The hearing aid of claim 1 wherein the elastomer includes an adhesion promotor.

29. The hearing aid of claim 1 wherein the elastomer includes a bonding enhancer.

30. A completely in-the-canal hearing device, the device comprising:
   (a) a hearing device body that is custom molded; and
   (b) an amplifier network comprising an electronic hearing aid circuit that includes a receiver and a receiver tube, transducers, and volume control, the amplifier network being at least partially embedded in the body, wherein:

the body is made of a soft-solid elastomer and the body has a Durometer Hardness, Shore A, of less than 40 points.

31. The hearing device of claim 30, wherein the elastomer is a bondable silicone.

32. The hearing device of claim 30 wherein the elastomer is Factor II A588.

33. The hearing device of claim 30 wherein the elastomer is Factor II A588T.

34. The hearing device of claim 30 wherein the elastomer is Factor II A588U.

35. The hearing device of claim 30 wherein the elastomer includes an adhesion promotor.

36. The hearing device of claim 30 wherein the elastomer includes a bonding enhancer.

37. A hearing device that is worn inside a human ear canal, the device comprising:

(a) a body that includes an outer surface material and a filler material;

(b) an amplifier network contained within the filler material, the amplifier network comprising an electronic hearing aid circuit that includes a receiver and a receiver tube, transducers, and volume control, wherein:

the outer surface material and the filler material have different hardness values, at least one being between 1 and 7 Durometer Shore A, and the filler material being sufficiently thick to at least partially encapsulate the amplifier network to eliminate air spaces theft could otherwise cause an internal air conduction path between a receiver and a microphone in the amplifier network.

38. The hearing device of claim 37 wherein the elastomer is a bondable silicone.

39. The hearing device of claim 37 wherein the elastomer is Factor II A588.

40. The hearing device of claim 37 wherein the elastomer is Factor II A588T.

41. The hearing device of claim 37 wherein the elastomer is Factor II A588U.

42. The hearing device of claim 37 wherein the elastomer includes an adhesion promotor.

43. The hearing device of claim 37 wherein the elastomer includes a bonding enhancer.

44. An ear-worn hearing device, the device comprising:

(a) a hearing device body sized and shaped to generally fit into a human ear canal; and (b) an electronic hearing circuit that includes at least a receiver assembly, said receiver assembly including a receiver and a receiver tube, at least a portion of said receiver assembly being embedded in the body, wherein: the body is made of a soft-solid elastomer and the body has a Durometer Hardness, Shore A, of less than 40 points.

45. The hearing device of claim 44 wherein the elastomer is a bondable silicone.

46. The hearing device of claim 44 wherein the elastomer is Factor II A588.

47. The hearing device of claim 44 wherein the elastomer is Factor II A588T.

48. The hearing device of claim 44 wherein the elastomer is Factor II A588U.

49. The hearing aid of claim 44 wherein the elastomer includes an adhesion promotor.

50. The hearing aid of claim 44 wherein the elastomer includes a bonding enhancer.

* * * * *